United States Patent [19]
Lew

[11] Patent Number: 5,152,181
[45] Date of Patent: Oct. 6, 1992

[54] MASS-VOLUME VORTEX FLOWMETER

[76] Inventor: Hyok S. Lew, 7890 Oak St., Arvada, Colo. 80005

[21] Appl. No.: 642,664

[22] Filed: Jan. 17, 1991

Related U.S. Application Data

[63] Continuation-in-part of Ser. No. 467,486, Jan. 19, 1990, Pat. No. 5,060,522.

[51] Int. Cl.$^5$ .............................................. G01F 1/86
[52] U.S. Cl. ................................ 73/861.02; 73/861.24
[58] Field of Search .......... 73/861.02, 861.03, 861.22, 73/861.24

[56] References Cited

U.S. PATENT DOCUMENTS

| | | | |
|---|---|---|---|
| 4,010,645 | 3/1977 | Herzl | 73/861.03 |
| 4,285,246 | 8/1981 | Kita | 73/861.03 |
| 4,448,081 | 5/1984 | Kolitsch et al. | 73/861.03 |
| 4,523,477 | 6/1985 | Miller | 73/861.02 |
| 5,060,522 | 10/1991 | Lew | 73/861.02 |

Primary Examiner—Herbert Goldstein

[57] ABSTRACT

A flowmeter has a vortex generating bluff body (102) disposed across the flow passage (106), a planar member (103) disposed immediate upstream of the bluff body (102) including a plurality of total pressure ports emerging through the leading edge of the planar member (103) and a plurality of static pressure ports emerging through the side faces of the planar member (103), and a vortex sensing device including a planar member (104) and one or two transducers (111 and 112), which flowmeter determines the mass and volume flow rates of the fluid and the density of the fluid from the dynamic pressure determined from the difference between the total and static pressures and the fluid velocity determined from the vortex shedding frequency.

11 Claims, 3 Drawing Sheets

MASS-VOLUME VORTEX FLOWMETER

This is a continuation-in-part application to U.S. patent application Ser. No. 07/467,486 entitled "Mass-Volume Vortex Flowmeter" filed on Jan. 19, 1990 and now U.S. Pat. No. 5,060,522, consequently, the priority of the invention described and claimed in the present application is based on the above-identified parent patent application.

One of the oldest and most widely practiced methods for measuring the speed of the fluid flow is the Pitot tube, that measures the dynamic pressure of fluid flow as the difference between the total pressure and the static pressure, wherein the total pressure, that is the sum of the dynamic pressure equal to one half of the fluid density times the square of the fluid velocity and the static pressure, is obtained by measuring the pressure exerted by the moving fluid through a small diameter pressure port open directly against the velocity of the moving fluid, while the static pressure is obtained by measuring the pressure exerted by the moving fluid through another small diameter pressure port open in a direction perpendicular to the velocity of the moving fluid. As the Pitot tube measures the dynamic pressure of the fluid flow instead of the mass flow rate or volume flow rate, the rate of the fluid flow can be determined from the data provided by the Pitot tube only if the Pitot tube is complemented by another measuring device such as a density meter or flowmeter measuring the mass or volume flow rate. In the past decade, a wonderful flow measuring technology known as the vortex shedding flowmeter has emerged, which technology has now become one of the most reliable and popular method of flow measurements. The vortex shedding flowmeter has a vortex generating bluff body of an elongated cylindrical shape disposed across a flow passage and a vortex detector measuring the frequency of vortex shedding from the vortex generating bluff body. As the vortex shedding frequency is linearly proportional to the fluid velocity in a wide range of Reynolds number that is equal to the ratio of the fluid velocity times the width of the bluff body to the kinematic viscosity of the fluid, the fluid velocity can be readily determined from the vortex shedding frequency once the coefficient of proportionality therebetween is determined empirically by calibrating the flowmeter. The vortex shedding flowmeter also measures the flow velocity with good accuracy at low Reynolds numbers where the linear relationship between the fluid velocity and the vortex shedding frequency becomes nonlinear, when the nonlinear relationship obtained empirically by calibrating the flowmeter at low Reynolds numbers supplements the linear relationship in the algorithm that converts the vortex shedding frequency to the fluid velocity. Since the vortex shedding flowmeter measures the fluid velocity in a highly reliable manner in a simple method and the Pitot tube measures the dynamic pressure of the fluid flow with good accuracy, a perfect multiple function flowmeter measuring the mass and volume flow rates as well as the fluid density can be provided by combining the vortex shedding flowmeter measuring the fluid velocity and the Pitot tube measuring the dynamic pressure of the fluid flow. Such a combination of the two instruments requires a novel and ingenious structural arrangement that structurally integrates the two instruments while preserving the original functions thereof without introducing any interference and altercation therebetween in the operating principles.

The primary object of the present invention is to provide a compound flowmeter comprising a combination of the vortex shedding flowmeter and Pitot tube, which combination measures the mass and volume flow rates of the fluid as well as the fluid density.

Another object is to provide the compound flowmeter defined by the above-presented primary object of the invention, wherein the vortex generating bluff body of an elongated cylindrical shape includes a planar upstream extension disposed parallel to the direction of the fluid flow, that includes at least one total pressure port emerging through the leading edge of the planar upstream extension and at least one static pressure port emerging through at least one of the two side surfaces of the planar upstream extension.

A further object is to provide the compound flowmeter wherein the vortex detector measuring the frequency shedding from the bluff body is incorporated into the bluff body.

Yet another object is to provide the compound flowmeter wherein the vortex detector measuring the vortex shedding frequency is disposed downstream of the bluff body.

Yet a further object is to provide the compound flowmeter wherein the vortex detector comprises a pair of sensors detecting the fluid dynamic force generated by the vortices and the inertia force generated by the structural vibration of the flowmeter, whereby the electrical signals from the pair of sensors can be combined in such a way that the noise signal associated with the structural vibration is cancelled therebetween and a refined signal representing the vortex shedding from the bluff body is obtained.

Still another object is to provide the compound flowmeter comprising a combination of the vortex shedding flowmeter and Pitot tube, wherein at least one total pressure port emerges through the leading edge of a planar upstream extension extending from the blunt upstream face of the vortex generating bluff body in a direction opposite to the velocity of the fluid, and at least one static pressure port emerges through at least one of the two side faces of the bluff body.

Still a further object is to provide a compound flowmeter comprising a combination of the vortex shedding flowmeter and Pitot tube, wherein at least one Pitot tube pointing directly against the direction of the fluid flow approaching the vortex generating bluff body is incorporated into a planar upstream extension extending from the blunt upstream face of the bluff body in a direction opposite to the velocity of the fluid.

These and other objects of the present invention will become clear as the description of the present invention progresses.

FIG. 2 illustrates another cross section of the embodiment shown in FIG. 1.

Figure 1:
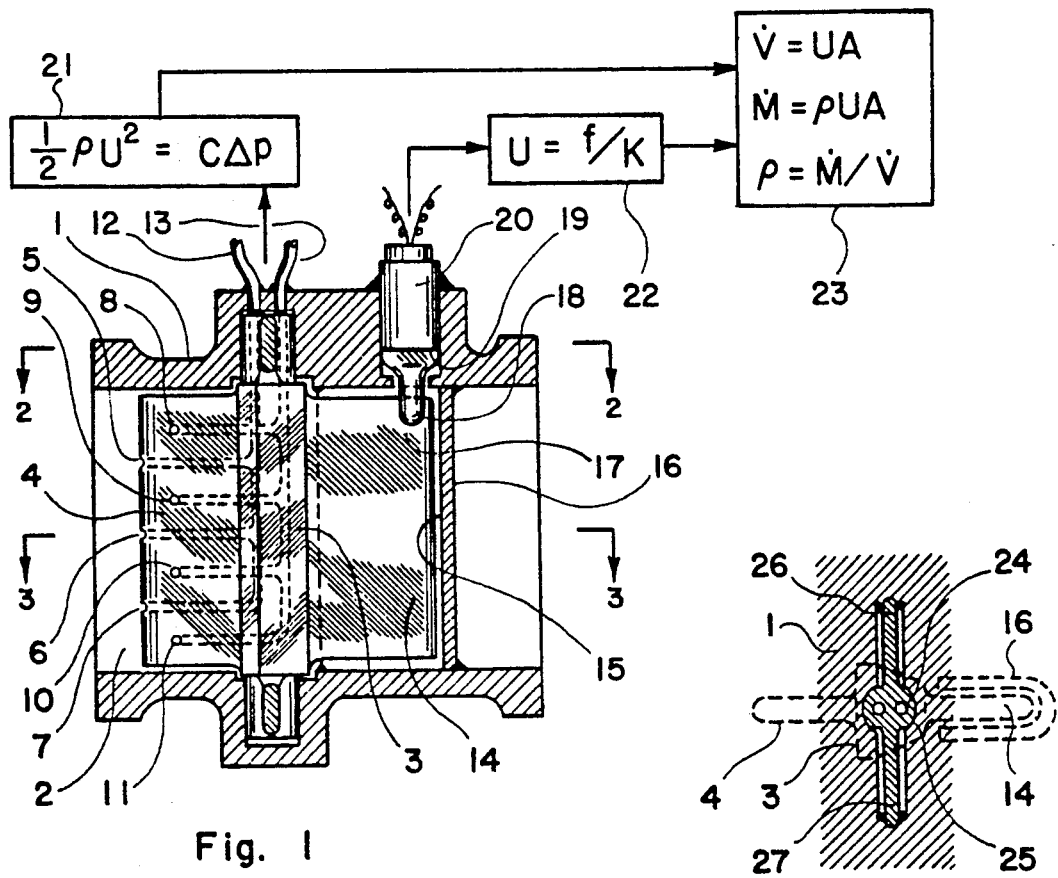
FIG. 1 illustrates a cross section of an embodiment of the compound flowmeter comprising a combination of the vortex shedding flowmeter and Pitot tube as well as the data flow diagram describing the operating principles thereof.

In FIG. 1 there is illustrated a cross section of an embodiment of the compound flowmeter of the present invention comprising a combination of the vortex shedding flowmeter and Pitot tube. The flowmeter body 1 includes a flow passage 2 extending therethrough. A vortex generating bluff body 3 is disposed across the flow passage 2, wherein the bluff body 3 is secured to the flowmeter body 1 at the two extremities thereof. The bluff body 3 has a planar upstream extension 4 disposed generally parallel to the central axis of the flow passage 2 and extending from the upstream side of the bluff body 3, which planar upstream extension 4 includes a plurality of total pressure ports 5, 6, 7, etc. emerging through the leading edge thereof, and a plurality of static pressure ports 8, 9, 10, 11, etc. emerging through one or both side surfaces of the planar upstream extension 4. The total pressure ports 5, 6, 7, etc. disposed following the leading edge of the planar upstream extension 4 are connected to the total pressure conduit 12, while the static pressure ports 8, 9, 10, 11, etc. disposed following a line parallel to the leading edge of the planar upstream extension 4 are connected to a static pressure conduit 13. The two pressure conduits 12 and 13 are connected to a differential pressure measuring device determining the difference between the total and static pressure, which differential pressure measuring device is not shown as such a device of one or other versions is well known to those skilled in the art of the pressure measurement. The bluff body 3 also includes a planar downstream extension 14 disposed generally parallel to the central axis of the flow passage 2 and extending from the downstream side of the bluff body 3, which downstream planar extension 14 extends into a planar groove or cavity 15 includes in a planar pressure shield 16 secured to the flowmeter body 1 at the two extremities thereof. A deflective potion 17 of the planar downstream extension 14 is connected to a force receiving member 18 extending from an end wall 19 of the transducer container vessel 20 affixed to the flowmeter body 1.

In FIG. 2, there is illustrated a cross section of one extremity of the bluff body 3 anchored to the flowmeter body 1, which cross section is taken along plane 2—2 as shown in FIG. 1. In this particular illustrated embodiment, one or both extremities of the bluff body 3 include a partially circular cylindrical section 24 engaging a matched partially circular cylindrical bearing surface 25 included in the flowmeter body 1, wherein the partially circular cylindrical extremity 24 of the bluff body 3 has a pair of planar bias spring members 26 and 27 laterally extending therefrom respectively in two opposite directions perpendicular to the central axis of the flow passage and anchored to the flowmeter body 1 at the extremities thereof. This arrangement of securing the extremity of the bluff body 3 to the flowmeter body 1 prevents the bluff body 3 from lateral deflection, while allowing a minute amount of pivoting movement thereof about the longitudinal axis of the bluff body, which pivoting movement enhances the deflective movement of the planar downstream extension 14 under the fluctuating fluid pressure associated with the vortex shedding from the bluff body 3. As an alternative design, one or both extremities of the bluff body 3 may be rigidly affixed to the flowmeter body 1, or supported by the flowmeter body 1 in a free-pivoting arrangement without the planar bias spring members, or one extremity with and the other extremity without the planar bias spring member.

Figure 3:
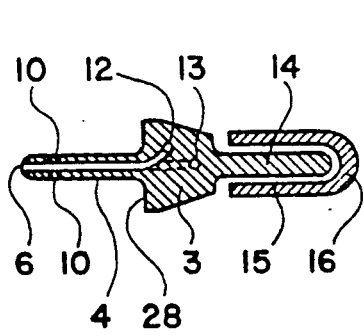
FIG. 3 illustrates a further cross section of the embodiment shown in FIG. 1.

In FIG. 3 there is illustrated a cross section of the combination of the bluff body 3 and the planar pressure shield 16, which cross section is taken along plane 3—3 as shown in FIG. 1. The bluff body 3 has a nonstreamlined cross section having a blunt upstream face 28, from which the planar upstream extension 4 extends, while the planar downstream extension 14 extends from the downstream face of the bluff body 3 and extends into the planar groove or cavity 15 included in the planar pressure shield 16 in an arrangement including spacing therebetween. The total pressure ports 6, etc. emerging through the leading edge of the planar upstream extension 4 are connected to the total pressure conduit 12, while the static pressure ports 10 etc. emerging through the two opposite side faces of the planar upstream extension 4 are connected to the static pressure conduit 13.

Figure 12:
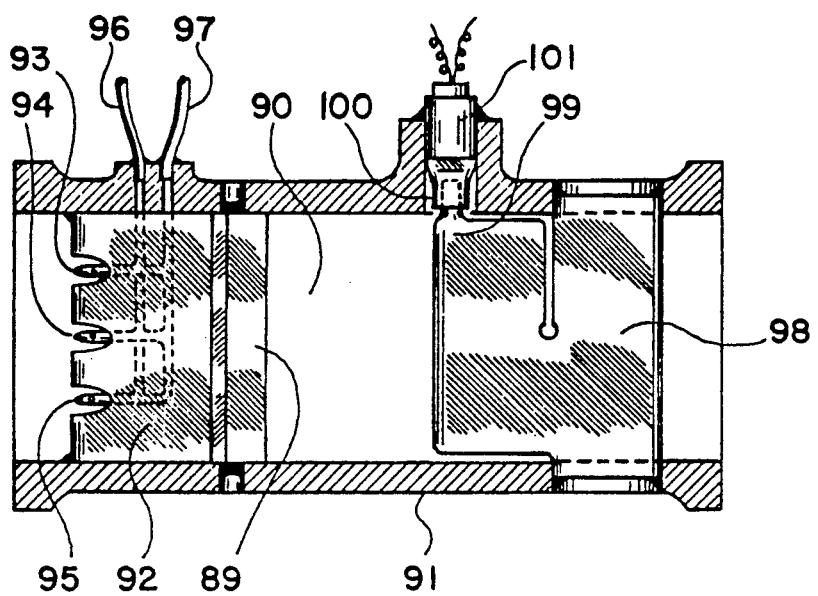
FIG. 12 illustrates a cross section of still a further embodiment of the compound flowmeter.

The compound flowmeter illustrated and described in conjunction with FIGS. 1, 2 and 3 operates on the following principles: The difference between the total and static pressure respectively transmitted through the two pressure conduits 12 and 13 is either equal to the dynamic pressure $\frac{1}{2}\rho U^2$ or proportional thereto depending on the arrangement of the total and static pressure ports relative to the dimension and location of the bluff body 3, where $\rho$ is the fluid density and U sis the fluid velocity. The coefficient of the proportionality C which may be unity or may not be unity can be empirically determined by calibrating the flowmeter and is stored in the memory bank of the data processor 21 that determines the dynamic pressure $\frac{1}{2}\rho U^2$ from the differential pressure $\Delta p$. The vortices shed from the two opposite side faces of the bluff body 3 in an alternating mode create fluctuating fluid pressures at the two opposite side faces of the bluff body in an alternating mode, that exerts an alternating lateral pressure loading on the combination of the bluff body 3 and the planar downstream extension 14 thereof, which alternating pressure loading transmitted to the transducer assembly contained within the transducer container vessel 20 by the force receiving member 18 generates an alternating electrical signal oscillating at the same frequency as that of the vortex shedding. As the fluid velocity U is proportional to the vortex shedding frequency f, the data processor 22 with a stored value of the coefficient of proportionality K determined empirically by calibrating the flowmeter determines the fluid velocity U from the vortex shedding frequency f, wherein the relationship therebetween may be linear or nonlinear. The data processor 23 determines the volume flow rate V by multiplying the cross sectional are of the flow passage A to the fluid velocity U and the mass flow rate M by multiplying the cross sectional area A to the ratio of the dynamic pressure to one half of the fluid velocity. The data processor 23 may also determine the fluid density as the ratio of the mass flow rate M to the volume flow rate V. The planar upstream extension 4 is employed to tap the total and static pressures from the fluid flow that is not altered by the bluff body 3 and yet at the effectively common cross section of the flow passage whereat the bluff body generates the vortices. A plurality of the total and static pressure ports distributed along the length of the planar upstream extension 4 provides average values of the total and static pressures across the cross section of the flow passage, which averaged values provide more accurate information on the flow rates when combined with information provided by the vortex shedding frequency that also represents averaged fluid velocity across the cross section of the flow passage. In an alternative embodiment, only one set of total and static pressure ports may be employed in place of the multiple sets distributed following the length of the bluff body. It is generally preferred to balance the combination of the bluff body 3 and the planar up- and downstream extensions 4 and 14 about the longitudinal central axis of the bluff body, whereby the deflection of the planar downstream extension 14 produced by the structural vibration of the flowmeter body is kept at the possible minimum value. The planar pressure shield 16 is employed to expose the two opposite side faces of the planar downstream extension 14 to the fluctuating fluid pressures existing at the two opposite side faces of the bluff body 3 in the same phase angle for the entire combination of the bluff body 3 and the planar downstream extension 14 thereof. It should be understood that the total and static pressure ports included in the embodiment shown in FIG. 1 may be replaced by the Pitot tubes incorporated into the planar upstream extension of the bluff body as shown in FIG. 12.

Figure 4:
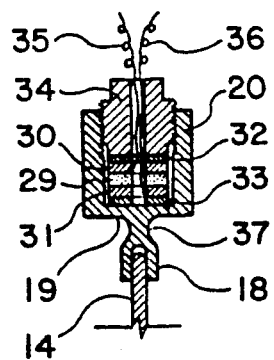
FIG. 4 illustrates a cross section of an embodiment of the transducer employed n the construction of the vortex dector included in the compound flowmeter.

In FIG. 4 there is illustrated a cross section of an embodiment of the transducer assembly contained within the transducer container vessel 20 shown in FIG. 1, which cross section is taken along a plane including the central axis of the flow passage as well as the central axis of the transducer assembly. The transducer container vessel 20 includes a cylindrical cavity housing a piezo electric disc element 29 sandwiched between a pair of electrode discs 30 and 31, and a pair of insulator discs 32 and 33, which combination of a stacked construction is pressed against the deflective end wall 19 by a plug 3 threadedly engaging the open end of the transducer container vessel 20. The electromotive force generated by the piezo electric element 29 is transmitted by the lead wires 35 and 36 extending through the threaded plug 34. The deflective end wall 19 includes a reinforcing rib 37 disposed diametrically thereacross on a reference plane including the central axis of the flow passage as well as the central axis of the force receiving member 18 anchored thereto and extending therefrom.

Figure 5:
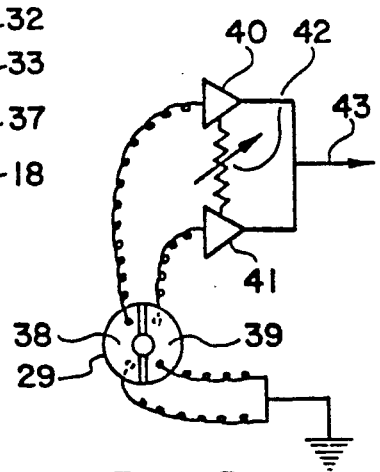
FIG. 5 illustrates a plan view of an embodiment of the piezo electric disc element includes in the transducer shown in FIG. 4 as well as an embodiment of the electric circuit conditioning the signal generated by the piezo electric disc element.

In FIG. 5 there is illustrated a plan view of the piezo electric disc element 29 included in the transducer assembly shown in FIG. 4. Each of the two faces of the piezo electric disc element 29 includes a pair of semi-circular electrodes 38 and 39 respectively disposed on the two opposite sides of the reference plane. The two electrodes respectively included on the two opposite faces of the piezo electric disc element and respectively disposed on the two opposite sides of the reference plane are respectively connected to two amplifiers 40 and 41 with a means 42 for balancing the relative signal strength therebetween. The other electrodes not connected tot he amplifiers 40 or 41 are grounded. The deflective movement of the planar downstream extension 14 alternatively compressed and decompresses the two opposite halves of the piezo electric disc element 29 located on the two opposite sides of the reference plane, which action generates two alternating electromotive forces therefrom in a common phase, which two electromotive forces respectively supplied to the two amplifiers 40 and 41 are combined by using the signal balancing means 42 in such a way that the noise signals generated by the mechanical vibrations occuring in directions parallel to the reference plane are cancelled therebetween and a refined alternating signal 43 oscillating at the vortex shedding frequency is obtained. It should be mentioned that other types of the transducer such as a capacitive, inductive, resistive strain gauge, or fiber optics transducer may be used in place of the piezo electric transducer shown and described in conjunction with FIGS. 4 and 5.

Figure 6:
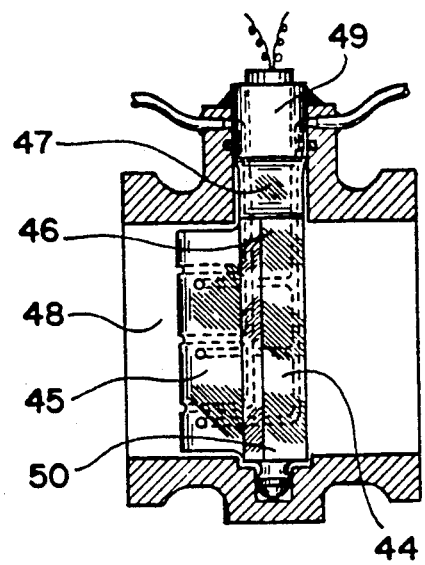
FIG. 6 illustrates a cross section of another embodiment of the compound flowmeter.

In FIG. 6 there is illustrated a cross section of another embodiment of the compound flowmeter, that has a combination of the bluff body 44 and the planar upstream extension 45, which combination includes the total and static pressure ports arranged in the essentially same manner as those shown and described in conjunction with FIGS. 1 and 3. One extremity 46 of the bluff body 44 has an extension 47, preferably of a planar geometry disposed on the reference plane commonly including the central axis of the flow passage 48 and the central axis of the transducer assembly, that is anchored to the deflective end wall of the transducer container 49 including the transducer assembly shown and described in conjunction with FIGS. 4 and 5, or other types of transducers, while the other extremity 50 is simply supported by the flowmeter body. This embodiment operates on the same principles as those explained in conjunction with FIGS. 1 and 2. Of course, the total and static pressure ports employed in this particular illustrative embodiment may be replaced with the Pitot tubes as shown in FIG. 12.

Figure 7:
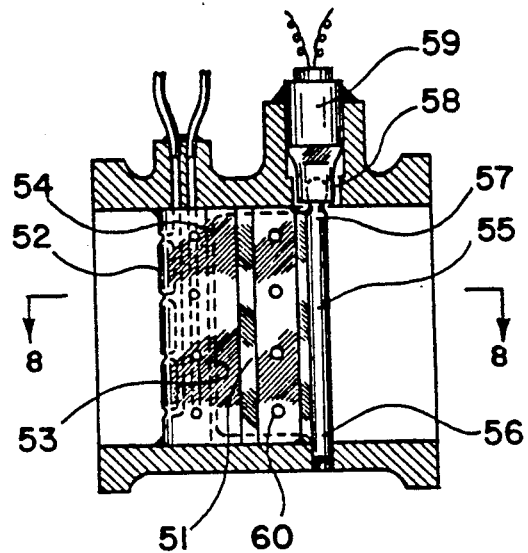
FIG. 7 illustrates a cross section of a further embodiment of the compound flowmeter.

In FIG. 7 there is illustrated a cross section of a further embodiment of the compound flowmeter, that includes the combination of the bluff body 51 and the planar upstream extension 52 having essentially the same total and static pressure ports as those included in the embodiment shown in FIG. 1 and 3, which combination now rigidly secured to the flowmeter body at the two extremities thereof includes a planar cavity or groove 53 extending and emerging through the downstream side face of the bluff body 51, that is disposed parallel to the central axis of the flow passage. A pressure sensing planar member 54 laterally extending form an elongated support 55 extends into the planar groove or cavity 53 with a space therebetween. One extremity 56 of the elongated support 55 is supported by the flowmeter body, while the other extremity 57 is connected to the force receiving member 58 of a transducer assembly 59. Each of the two side walls of the planar groove or cavity 53 may include a plurality of pressure communicating holes 60 disposed therethrough and emerging through each of the two opposite side faces of the bluff body 51. The total and static pressure ports included in the particular embodiment shown may be replaced by the Pitot tubes as shown in FIG. 12.

Figure 8:
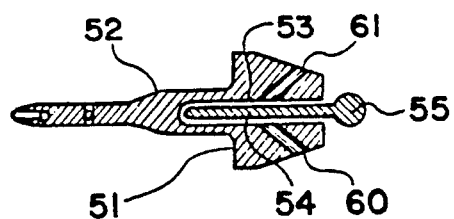
FIG. 8 illustrates another cross section of the embodiment shown in FIG. 7.

In FIG. 8 there is shown another cross section of the embodiment shown in FIG. 7, which cross section is taken along plane 8—8 as shown in FIG. 7. The flowmeter body is not shown for the brevity of illustration. The combination of the planar cavity 53 and the pressure sensing planar member 54 extends into the planar upstream extension 52 of the bluff body 51 in this particular illustrative embodiment, which combination may be limited to the bluff body 51 itself in an alternative design. As the two opposite sides of the pressure sensing planar member 54 are respectively exposed to the fluctuating fluid pressures existing at the two opposite side faces of the bluff body 51 through the downstream side opening of the planar cavity or groove 53, the pressure communicating holes or slots 60 and 61 disposed through the two side walls of the planar cavity or groove 53 can be excluded in a design alternative to the particular embodiment shown and described. It should be mentioned that the two sets of the pressure communicating holes 60 and 61 can be replaced by two elongated slotted openings disposed parallel to the upstream face of the bluff body 51.

Figure 9:
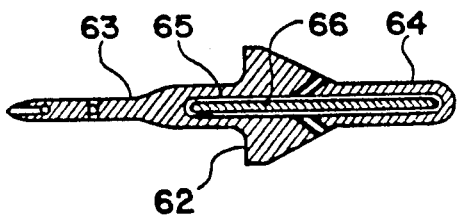
FIG. 9 illustrates a cross section of yet another embodiment of the compound flowmeter having a construction similar to that shown in FIG. 8.

In FIG. 9 there is illustrated a cross section of the bluff body 62 with the planar up- and downstream extensions 63 and 64, which is employed in the construction of yet another embodiment of the compound flowmeter. The combination of the bluff body 62 and the planar up- and downstream extensions 63 and 64 includes a planar cavity 65 housing a pressure sensing planar member 66 that is secured to the bluff body 62 or the flowmeter body at one extremity thereof and connected to the force receiving member of a transducer assembly at the other extremity in an arrangement similar to that shown in FIG. 1 or 7.

Figure 10:
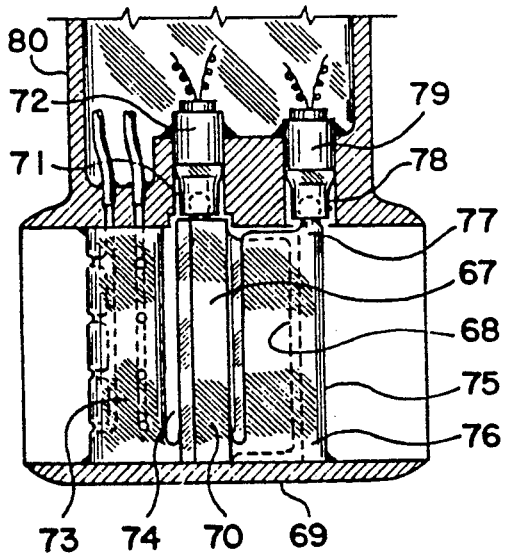
FIG. 10 illustrates a cross section of yet a further embodiment of the compound flowmeter, that is an insertion type version of the compound flowmeter.

In FIG. 10 there is illustrated a cross section of yet a further embodiment of the compound flowmeter, that is a modified version of the embodiment shown in FIG. 1. In this embodiment, the bluff body 67 with a planar downstream extension 68 is secured to the flowmeter body 69 at only one extremity 70 thereof, while the other extremity, that is unsupported, is connected to the force receiving member 71 of a transducer 72. The planar upstream extension 73 including the total and static pressure ports is now separated from the bluff body 67 by a slit 74 extending partially or entirely across the cross section of the flow passage and secured to the flowmeter body 69 at both extremities thereof, which arrangement enhances transmission of the fluid dynamic force experienced by the combination of the bluff body 67 and the planar downstream extension 68 thereof to the transducer 72. The pressure shield 75 shielding the planar downstream extension 68 of the bluff body 67 as shown in FIG. 3 has one extremity 76 secured to the flowmeter body 69 and the other extremity connected to the force receiving member 78 of another transducer 79. The flowmeter body is supported by an elongated support 80 having a streamlined cross sectional geometry, that is anchored to a supporting structure at the extremity thereof and extending into the midstream of the fluid flow. The two electrical signals respectively generated by the two transducers 72 and 79 are combined by using an electric circuit similar to that shown in FIG. 5, which cancels the noise generated by the mechanical vibration of the flowmeter between the two electrical signals and provides a noise-free vortex signal. This noise eliminating feature included in the insertion type compound flowmeter shown in FIG. 10 eliminates the noise generated by the flexural vibration of the combination of the flowmeter body 69 and the elongated support 80, which noise would swap the vortex-generated signal otherwise. Of course, the total and static pressure ports included in the planar upstream extension 73 may be replaced by Pitot tubes as shown in FIG. 12. In applications involving little mechanical vibrations, the embodiments shown in FIGS. 1, 6, 7 or 9 may be modified to an insertion type compound flowmeter including the elongated support 80 as shown in FIG. 10.

Figure 11:
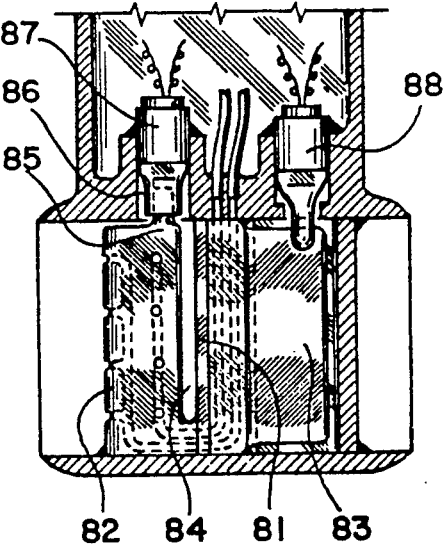
FIG. 11 illustrates a cross section of still another embodiment of the compound flowmeter having a construction similar to that shown in FIG. 10.

In FIG. 11 there is illustrated a cross section of still another embodiment of the compound flowmeter, that is particularly adapted to the construction of another version of the insertion type compound flowmeter. This embodiment has the combination of the bluff body 81 and the planar up- and downstream extensions 82 and 83 having a construction similar to that shown and described in conjunction with FIGS. 1, 2, and 3 with one exception that is the partial separation of the planar upstream extension 82 from the bluff body 81 by the elongated slit 84 extending to one extremity 85 thereof, that is not supported and now connected to the force receiving member 86 of a second transducer 87. The two electrical signals respectively generated by the two transducers 87 and 88 are combined by using a noise cancelling electric circuit such as that shown in FIG. 5.

In FIG. 12 there is illustrated a cross section of still a further embodiment of the compound flowmeter. The vortex generating bluff body 89 of an elongated cylindrical shape disposed across a cross section of the flow passage 90 and secured to the flowmeter body 91 at the two extremities thereof includes a planar upstream extension 92 that has a plurality of Pitot tubes 93, 94, 95, etc. pointing directly against the flow velocity of fluid, which are respectively disposed in a plurality of cut-outs includes in the leading edge of the planar upstream extension 92 and incorporated into the planar upstream extension 92. The total and static pressure ports included in the plurality of the Pitot tubes are respectively merged to the total and static pressure conduits 96 and 97. The cut-outs included in the leading edge of the planar upstream extension 92, which accomodate the Pitot tube heads extending from the planar upstream extension 92, enhance the axisymmetric flow of the fluid moving by the Pitot tube head, while the planar upstream extension 92 enhances the planar symmetric flow of the fluid moving by the bluff body 89. The Pitot tube heads disposed in the cut-outs are also protected from impact by the debris entrained in the fluid stream as the leading edge of the planar upstream extension 92 acts like a bumper. A vortex sensing planar member 98 is disposed across another cross section of the flow passage downstream of the bluff body 89 on a plane generally parallel to the central axis of the flow passage as well as the longitudinal axis of the bluff body 89, which vortex sensing planar member supported by the flowmeter body 91 has a deflective portion 99 connected to the force receiving member 100 of a transducer 101 affixed to the flowmeter body 91. This embodiment of the compound flowmeter operates on the same principles as those described in conjunction with FIGS. 1 and 3. Of course, the plurality of Pitot tubes 93, 94, 95, etc. may be replaced with the total and static pressure ports such as those employed in the embodiment shown in FIG. 1 or 7.

Figure 13:
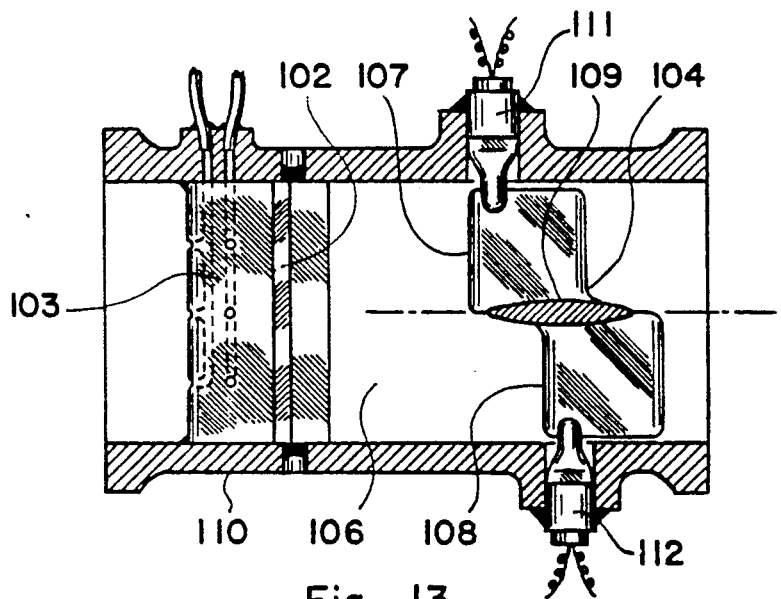
FIG. 13 illustrates a cross section of yet still another embodiment of the compound flowmeter.

In FIG. 13 there is illustrated a cross section of yet still another embodiment of the compound flowmeter, that comprises the combination of the vortex generating bluff body 102 and the planar upstream extension 103 including the total and static pressure ports, and a vortex sensing planar member 104 with an off-set leading edge disposed downstream of the bluff body 102 on a plane generally parallel to the central axis of the flow passage 106 as well as to the longitudinal axis of the bluff body 102. The leading edges 107 and 108 of the two halves of the vortex sensing planar member 104 are off-set from one another by a distance equal to one half or an integer plus one half times the wave length of sinuating streamlines created by the vortices shed from the bluff body 102. The vortex sensing planar member 104 includes a pair of planar lateral extension 109 and another one not shown because it is located on the other side of the vortex sensing planar member 104, which lateral planar extensions disposed on a plane including the central axis of the flow passage 106 and perpendicular to the longitudinal axis of the bluff body 102 respectively extend from the midsection of the vortex sensing planar member 104 in two opposite directions and are secured to the flowmeter body 110 at the extremities thereof. This arrangement allows a minute amount of pivoting movement of the vortex sensing planar member 104 about an axis generally coinciding with the central axis of the flow passage, while preventing lateral displacement of the vortex sensing planar member 104. The extremities of the two opposite halves of the vortex sensing planar member 104 are respectively connected to a pair of transducers 110 and 111. The two electrical signals respectively generated by the two transducers 110 and 111 are combined by using a noise cancelling electric circuit such as that shown in FIG. 5. Of course, in an alternative design, one of the two transducers 110 and 111 may be omitted, wherein the vortex sensing planar member 104 should be balanced in the mass or moment of inertia distribution about the pivot axis coinciding with the central axis of the flow passage. The embodiments shown in FIG. 12 or 13 can be converted to an insertion type compound flowmeter by including an elongated support that supports the flowmeter disposed in the midstream of the fluid flow in an overhanging arrangement. The combination of the vortex generating bluff body and the planar upstream extension thereof included in the embodiments shown in FIGS. 12 and 13 can be interchanged.

Figure 14:
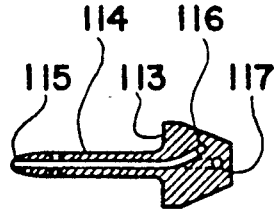
FIG. 14 illustrates a cross section of an embodiment of the vortex generating bluff body with a planar upstream extension including the total and static pressure ports.

In FIG. 14 there is illustrated a cross section of an embodiment of the combination of the vortex generating bluff body 113 and the planar upstream extension 114 including the total and static pressure ports. The planar upstream extension 114 as a generally constant thickness and a round leading edge 115. The total and static pressure conduits 116 and 117 are included in the bluff body 113.

Figure 15:
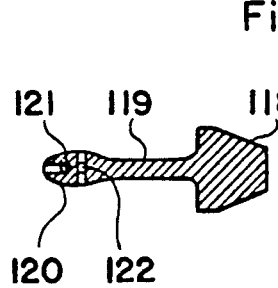
FIG. 15 illustrates a cross section of another embodiment of the vortex generating bluff body with a planar upstream extension including the total and static pressure ports.

In FIG. 15 there is illustrated a cross section of another embodiment of the combination of the bluff body 118 and the planar upstream extension 119 that has a round leading edge 120 with an increased thickness that includes the total and static pressure conduits 121 and 122.

Figure 16:
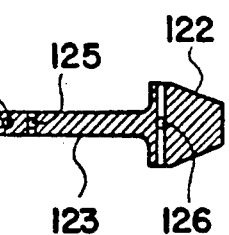
FIG. 16 illustrates a cross section of a further embodiment of the vortex generating bluff body with a planar upstream extension including the total and static pressure ports.

In FIG. 16 there is illustrated a cross section of a further embodiment of the combination of the bluff body 122 and the planar upstream extension 123, which has the same cross section as that of the embodiment shown in FIG. 14 with a few exceptions. The total and static pressure conduits 124 and 125 are now included in the planar upstream extension 123 instead of the bluff body 122. The static pressure ports emerging through the two opposite side faces of the planar upstream extension 123 and connected to the static pressure conduit 125 may be replaced by the static pressure ports emerging through the two opposite side faces of the bluff body 122 and connected to the static pressure port 126, which modification provides an added capability of measuring low velocity fluid flows in exchange for giving up the reliable and simple algorithm that determines the dynamic pressure from the difference between the total and static pressures. The coefficient of proportionality C appearing in the data processor 21 shown in FIG. 1 is no longer a constant when the static pressure ports are disposed on the side faces of the bluff body.

It should be understood that the physical and mathematical principles constituting the basis of the operating principles of the present invention are the combination of two data respectively derived from the difference between the total and static pressures, and from the vortex shedding frequency. Therefore, the present invention is not limited to the particular method for measuring the vortex shedding frequency and, consequently, the present invention should include other combinations of the total and static pressure measurement and vortex shedding frequency measurement using vortex sensors operating on other principles such as the ultrasonic, capacitive, hot wire, strain gauge, or pressure sensing vortex sensors. While the principles of the prevent inventions have now been made clear by the illustrative embodiments, there will be many modifications of structures, arrangements, proportions, elements and materials, which are immediately obvious to those skilled in the art and particularly adapted to the specific working environments or operating conditions in the practice of the invention without departing from those principles. It is not desired to limit the inventions to the particular illustrative embodiments shown and described and accordingly, all suitable modifications and equivalents may be regarded as falling within the scope of the invention as defined by the claims which follow.

The embodiments of the invention, in which an exclusive property or priviledge is claimed, are defined as follows:

1. An apparatus for measuring flow rate of fluid comprising in combination:
   a) a body including a flow passage;
   b) a vortex generator of an elongated cylindrical shape with a blunt upstream face disposed across the flow passage, said vortex generator including a planar member disposed immediate upstream of the vortex generator on a plane generally parallel to the central axis of the flow passage and to the longitudinal axis of the vortex generator;

c) at least one stub cylindrical member disposed parallel to the central axis of the flow passage and extending from a portion of leading edge of the planar member in a direction opposite to the direction of fluid flow, said at least one stub cylindrical member including a total pressure port emerging through the tip thereof and connected to a first conduit for tapping the total pressure of the fluid flow and at least one static pressure port emerging through cylindrical surface thereof and connected to a second conduit for tapping the static pressure of the fluid flow;

d) means for measuring shedding frequency of vortices from the vortex generator; and e) means for measuring difference between the total and static pressure of the fluid flow.

2. A combination as set forth in claim 1 wherein said combination includes means for determining velocity of the fluid from the shedding frequency of vortices, and mass flow rate from ratio of the dynamic pressure of the fluid flow determined form the defference between the total and static pressures to the velocity of the fluid.

3. A combination as set forth in claim 2 wherein said combination includes means for determining density of the fluid from ratio of the mass flow rate to the velocity of the fluid.

4. A combination as set forth in claim 1 wherein said a potion of the leading edge of the planar member including the stub cylindrical member is indented in relative to other portion of the leading edge and the stub cylindrical member is disposed within a notch provided by said indenting.

5. A combination as set forth in claim 1 wherein said body includes an elongated support with an anchoring means included in the extremity thereof.

6. A combination as set forth in claim 1 wherein said means for measuring shedding frequency of vortices comprises a first means for detecting fluctuating fluid dynamic force generated by vortices shed from the vortex generator, and a second means for detecting inertia force generated by structural vibration of the body, whereby two electrical signals respectively generated by said first and second means are combined to cancel noise generated by the structural vibration therebetween and obtain a resultant signal representing vortex shedding from the vortex generator.

7. A combination as set forth in claim 1 wherein said means for measuring shedding frequency of vortices comprises a vortex sensing planar member disposed downstream of the vortex generator on a plane parallel to the central axis of the flow passage and to the longitudinal axis of the vortex generator in an arrangement allowing at least a minute amount of pivoting movement of the vortex sensing planar member about a pivot axis parallel to the central axis of the flow passage and passing through a midsection of the vortex sensing planar member, and a pair of transducer means respectively connected to two opposite extremities of the vortex sensing planar member, wherein leading edges of two halves of the vortex sensing planar member respectively located on two opposite sides of a plane including the pivot axis are off set from one another by a distance generally equal to a noninteger times the wave length of sinuating stream lines created by the vortices shed from the vortex generator; whereby two electrical signals respectively generated by the pair of transducer means are combined to cancel noise generated by structural vibration of the body and obtain a resultant signal representing the vortex shedding from the vortex generator.

8. An apparatus for measuring flow rate of fluid comprising in combination:

a) a body including a flow passage:

b) a vortex generator of an elongated cylindrical shape with a blunt upstream face disposed across the flow passage, said vortex generator including a planar member disposed immediately upstream of the vortex generator on a plane generally parallel to the central axis of the flow passage and to the longitudinal axis of the vortex generator;

c) at least one total pressure port emerging through leading edge of the planar member and connected to a first conduit for taping total pressure of the fluid flow;

d) at least one static pressure port emerging through at least one of the two side faces of the planar member and connected to a second conduit for tapping static pressure of the fluid flow;

e) means for measuring shedding frequency of vortices from the vortex generator, said means comprising a vortex sensing planar member disposed downstream of the vortex generator on a plane substantially parallel to the central axis of the flow passage and to the longitudinal axis of the vortex generator in an arrangement allowing at least a minute amount of pivoting movement of the vortex sensing planar member about a pivot axis parallel to the central axis of the flow passage and passing through a midsection of the vortex sensing planar member, and a pair of transducer means respectively connected to two opposite extremities of the vortex sensing planar member, wherein leading edges of two halves of the vortex sensing planar member respectively located on two opposite sides of a plane including the pivot axis are offset from one another by a distance generally equal to a noninteger times the wave length of sinuating streamlines created by the vortices shed from the vortex generator; whereby two electrical signals respectively generated by the pair of transducers are combined to cancel noise generated by structural vibrations of the body and obtain a resultant signal representing the vortex shedding from the vortex generator; and f) means for measuring difference between the total pressure and the static pressure of the fluid flow.

9. A combination as set forth in claim 8 wherein said combination includes means for determining velocity of the fluid from the shedding frequency of the vortices, and mass flow rate from ratio of the dynamic pressure of the fluid flow determined form the difference between the total and static pressures to the velocity of the fluid.

10. A combination as set forth in claim 9 wherein said combination includes means for determining density of the fluid from ratio of the mass flow rate to the velocity of the fluid.

11. A combination as set forth in claim 8 wherein said body includes an elongated support member with an anchoring means includes in the extremity thereof.

* * * * *